United States Patent
Refsell

(10) Patent No.: US 9,901,096 B2
(45) Date of Patent: Feb. 27, 2018

(54) HERBICIDE COMPOSITIONS FOR WEED CONTROL

(71) Applicant: Valent U.S.A., Corporation, Walnut Creek, CA (US)

(72) Inventor: Dawn Refsell, Lathrop, MO (US)

(73) Assignee: VALENT U.S.A., CORPORATION, Walnut Creek, CA (US)

(*) Notice: Subject to any disclaimer, the term of this patent is extended or adjusted under 35 U.S.C. 154(b) by 0 days.

(21) Appl. No.: 14/947,007

(22) Filed: Nov. 20, 2015

(65) Prior Publication Data
US 2016/0143284 A1    May 26, 2016

Related U.S. Application Data

(60) Provisional application No. 62/083,519, filed on Nov. 24, 2014.

(51) Int. Cl.
| | | |
|---|---|---|
| *A01N 37/48* | (2006.01) | |
| *A01N 43/84* | (2006.01) | |
| *A01N 43/40* | (2006.01) | |
| *A01N 43/82* | (2006.01) | |
| *A01N 43/90* | (2006.01) | |
| *A01N 43/38* | (2006.01) | |
| *A01N 41/06* | (2006.01) | |
| *A01N 43/80* | (2006.01) | |

(52) U.S. Cl.
CPC ............ *A01N 43/80* (2013.01); *A01N 37/48* (2013.01); *A01N 41/06* (2013.01)

(58) Field of Classification Search
None
See application file for complete search history.

(56) References Cited

U.S. PATENT DOCUMENTS

| | | |
|---|---|---|
| 2008/0153704 A1 | 6/2008 | Yamaji et al. |
| 2011/0015068 A1 | 1/2011 | Sievernich et al. |
| 2011/0065579 A1 | 3/2011 | Sievernich et al. |

FOREIGN PATENT DOCUMENTS

| | | | | |
|---|---|---|---|---|
| WO | WO 2009115434 A2 * | 9/2009 | ............ | A01N 43/80 |
| WO | WO 2009115490 A2 * | 9/2009 | ............ | A01N 43/80 |

OTHER PUBLICATIONS

International Search Report and Written Opinion issued by the International Bureau as PCT/US15/61790 dated Feb. 2, 2016.
Bruce et al., "Horseweed (*Conyza canadensis*) control in no-tillage soybeans (*Glycine max*) with preplant and preemergence herbicides", Weed Technology, 1990, vol. 4, pp. 642-647.

* cited by examiner

*Primary Examiner* — John Pak
*Assistant Examiner* — Daniel Branson
(74) *Attorney, Agent, or Firm* — Wood, Phillips, Katz, Clark & Mortimer

(57) ABSTRACT

The present invention is directed to compositions containing herbicidal mixtures of a plant cell membrane disruptor herbicide selected from the group consisting of a diphenylether, N-phenyl-phthalimide, triazolinone, and bipyridylium, and pyroxasulfone. The present invention is further directed to methods of increasing the activity of a plant cell membrane disruptor herbicide with the compositions of the present invention.

7 Claims, No Drawings

HERBICIDE COMPOSITIONS FOR WEED CONTROL

FIELD OF THE INVENTION

The present invention relates to agricultural compositions useful for controlling weeds, and methods of use thereof.

BACKGROUND OF THE INVENTION

Unwanted plants, such as weeds, reduce the amount of resources available to crop plants and can have a negative effect on crop plant yield. Commonly unwanted plants in crop plant environments include broadleaf plants and grasses.

Herbicides are used to kill unwanted plants, such as weeds, in crop plant environments. Herbicides are expensive, and their use may result in unintentional consequences such as groundwater contamination, environmental damage, herbicide-resistant weeds, and human and mammalian health concerns. It is therefore desirable to minimize the amount of herbicides applied to a crop-growing environment or any area in need of weed control.

Unwanted plants, such as weeds, may greatly reduce yields of crop plants. For example, a Horseweed infestation reportedly was responsible for an 80% reduction in soybean yields. Bruce, J. A., and J. J. Kells, *Horseweed (Conyza Canadensis) control in no-tillage soybeans (Glycine max) with preplant and preemergence herbcides*, Weed Technol. 4:642-647 (1990). Therefore, controlling weeds, and especially grasses and Horseweed, is a major concern of crop growers.

Further, Horseweed and other grasses are becoming resistant to the widely used herbicide glyphosate. As early as 2000, glyphosate resistant Horseweed was reported in Delaware. Glyphosate resistant Horseweed has since been reported in numerous states. Accordingly, there is a need for new products that can provide effective kill rates of glyphosate resistant Horseweed.

Weeds are also becoming resistant to herbicides that inhibit acetolactate synthase (ALS) and protoporphyrinogen oxidase (PPO). Horseweed has also been reported to be resistant to 2,4-D and dicamba. Accordingly, there is a need for new technology to control weeds that are resistant to commercially available herbicides.

In most fields throughout the Midwest and Mid-South, in-crop burndown applications are the only options for controlling weeds due to weather and timeliness of applications. Growers often find an active ingredient that is effective and the use it repeatedly. Eventually, the weeds become resistant to the active ingredient which leaves no alternatives for weed control other than mechanical removal. Mechanical removal of weeds requires extensive use of resources and is not an option for no-till or highly erodible land.

No-till farming has been increasing in popularity because it has many benefits, including decreased labor time and decreased soil erosion. However, one of the downsides of no-till farming is that weeds are harder to control in these areas because they are not subjected to tilling. Accordingly, there is an increasing need for alternative ways to handle weed infestation.

Pyroxasulfone (3-[[[5-(difluoromethoxy)-1-methyl-3 (trifluoromethyl)-1H-pyrazol-4-yl]methyl]sulfonyl]-4,5-dihydro-5,5-dimethylisoxazole) is an herbicide that has residual weed control. Pyroxasulfone, however, does not have post emergence weed control. Pyroxasulfone is commercially available in a mixture with flumioxazin (Fierce®, available from Valent U.S.A. Corporation).

Plant cell membrane disruptor herbicides' work by causing destruction of cell membranes which results in cell content leakage. These herbicides are primarily contact herbicides and have very limited translocation through the plant. Plant cell membrane disruptor herbicides can be sub-divided into diphenylethers, N-phenyl-phthalimides, and aryl triazolinones or photosystem I electron diverter such as bipyridyliums.

Diphenylether herbicides are inhibitors of photoporphyrinigen oxidase (PPO) within the plant. Diphenylether herbicides include fomesafen, lactofen, acifluorfen, and oxyfluorfen. When applied alone, diphenylether herbicides often yield unsatisfactory weed control. To overcome this, diphenylether herbicides are sometimes applied with S-metochlor or acetochlor to increase effectiveness. However, the efficacy of such combinations is often not satisfactory and high application rates are still required to achieve acceptable control of grass weeds and broadleaves. Moreover, the reliability of such combinations depends strongly on the weathering conditions and certain difficult to control weed species may escape. In addition, the herbicidal activity of these compositions persists only for a short time, which allows effective burndown only within a small timeframe prior to planting a crop. Moreover, the persistence of the herbicidal activity strongly depends upon the weathering conditions.

S-metolochlor and acetochlor are chloroacetanilide herbicides and work by interfering with enzymes in the gibberellin pathway. There is a current desire to minimize the use of these herbicides due to environmental concerns.

N-phenyl-phthalimide herbicides are also PPO inhibitors. N-phenyl-phthalimide herbicides include cinidon-ethyl, flumioxazin, and flumiclorac-pentyl.

Triazolinone herbicides are another class of PPO inhibitors. Triazolinone herbicides include azafenidin, carfentrazone-ethyl, and sulfentrazone.

Bipyridylium herbicides interfere with electron transfer and use uncoupled electrons to form reactive superoxides. Bipyridylium herbicides include paraquat and diquat.

U.S. Patent Application Publication No. 2011/0065579 discloses thousands of mixtures of herbicides, one of which is a mixture of glyphosate or glufosinate with pyroxasulfone in a ratio range of from 2000:1 to 1:10 which can also include a cell membrane disruptor. However, this publication fails to provide guidance within this broad range of acceptable amounts of the herbicides. Further, this publication does not teach or suggest narrower ratios that would produce acceptable results. In addition, this publication fails to suggest the synergy that Applicants discovered between plant cell membrane disruptors and pyroxasulfone.

U.S. Patent Application Publication No. 2011/0015068 discloses mixtures of pyroxasulfone with PPO inhibitors. This publication, however, fails to suggest synergistic ratios between pyroxasulfone and diphenylether, N-phenyl-phthalimide, triazolinone, or bipyridylium plant cell membrane disruptor herbicides.

Anthem® (available from FMC Corporation) is a product that comprises pyroxasulfone and fluthiacet, a PPO inhibitor. Fluthiacet, however, has had limited postemergence herbicidal activity in addition to having no postemergence herbicidal activity as it pertains to the pyroxasulfone component.

In summary, there is a need for a composition that reduces the amount of herbicides necessary to obtain sufficient weed control while minimizing the harm to crop plants. As more weeds become resistant to herbicides, alternative compositions with high weed control are desired. Further, as no-till farming continues to increase in popularity, there is a greater need for effective herbicides. A composition with effective weed control and lower dosage rate will lead to increased crop plant yields, and decreased environmental, human, and mammalian health concerns.

SUMMARY OF THE INVENTION

In one aspect, the present invention is directed to agricultural compositions comprising a plant cell membrane disruptor herbicide selected from the group consisting of a diphenylether, N-phenyl-phthalimide, triazolinone, and bipyridylium, or an agriculturally acceptable salt thereof, and pyroxasulfone in a ratio of from about 1:1 to about 1:0.10.

In another aspect, the present invention is directed to methods for increasing the activity of a plant cell membrane disruptor, or an agriculturally acceptable salt thereof, comprising applying the agricultural compositions of the present invention to an area in need of weed control.

DETAILED DESCRIPTION OF THE INVENTION

It was surprisingly discovered that pyroxasulfone significantly increases the burndown activity of plant cell membrane disruptor herbicides when applied to weeds at synergistic ratios by as much as 3-fold compared to the plant cell membrane disruptor herbicides alone. This finding was unexpected because pyroxasulfone applied by itself has no post emergent control. Specifically, Applicants did not expect pyroxasulfone and fomesafen to provide almost 100% control of many common weeds in a crop plant field when the combination was applied to weeds larger than 6 inches in height. The treatment had a greater speed of activity as well as an increased efficacy.

Compositions of the present invention containing a synergistic ratio of the mixture of pyroxasulfone and a plant cell membrane disruptor herbicide selected from the group consisting of a diphenylether, N-phenyl-phthalimide, triazolinone, or bipyridylium, or an agriculturally acceptable salt thereof, will provide the end user with consistent herbicidal activity. The compositions will also provide residual weed and grass control.

In one embodiment, the present invention is directed to agricultural compositions comprising a plant cell membrane disruptor herbicide selected from the group consisting of a diphenylether, N-phenyl-phthalimide, triazolinone, and bipyridylium, or an agriculturally acceptable salt thereof, and pyroxasulfone in a ratio of from about 1:1 to about 1:0.10. In a preferred embodiment, the compositions contain from about 1:1 to about 1:0.13 of plant cell membrane disruptor:pyroxasulfone. In a more preferred embodiment, the compositions contain from about 1:0.8 to about 1:0.18 of plant cell membrane disruptor:pyroxasulfone. In a most preferred embodiment, the compositions contain from about 1:0.4 to about 1:0.26 of plant cell membrane disruptor:pyroxasulfone.

In an embodiment, the diphenylether is selected from the group consisting of fomesafen, lactofen, acifluorfen, and oxyfluorfen. In preferred embodiment, the diphenylether is fomesafen. In another preferred embodiment, the diphenylether is lactofen.

In yet another embodiment, the N-phenyl-phthalimide is selected from the group consisting of cinidon-ethyl, flumioxazin, and flumiclorac-pentyl.

In a further embodiment, the triazolinone is selected from the group consisting of azafenidin, carfentrazone-ethyl, and sulfentrazone.

In an embodiment, the bipyridylium is selected from the group consisting of diquat and paraquat.

In a further embodiment, the compositions of the present invention specifically exclude thiadiazoles, a class of PPO inhibitor herbicides that includes fluthicet.

In an embodiment, the present invention is directed to methods for increasing the activity of a plant cell membrane disruptor comprising applying agricultural compositions comprising a plant cell membrane disruptor herbicide selected from the group consisting of a diphenylether, N-phenyl-phthalimide, triazolinone, and bipyridylium, or an agriculturally acceptable salt thereof, and pyroxasulfone in a ratio of from about 1:1 to about 1:0.10. In a preferred embodiment, the compositions contain from about 1:1 to about 1:0.13 of plant cell membrane disruptor:pyroxasulfone. In a more preferred embodiment, the compositions contain from about 1:0.8 to about 1:0.18 of plant cell membrane disruptor:pyroxasulfone. In a most preferred embodiment, the compositions contain from about 1:0.4 to about 1:0.26 of plant cell membrane disruptor:pyroxasulfone.

In an embodiment, from about 50 to about 150 grams per hectare of pyroxasulfone is applied to the area in need of weed control. In a preferred embodiment, from about 70 to about 110 grams per hectare of pyroxasulfone is applied to the area in need of weed control. In a more preferred embodiment, from about 80 to about 100 grams per hectare of pyroxasulfone is applied to the area in need of weed control. In a most preferred embodiment, from about 85 to about 95 grams per hectare of pyroxasulfone is applied to the area in need of weed control.

In an embodiment, from about 132 to about 527 grams per hectare of plant cell membrane disruptor is applied to the area in need of weed control. In a preferred embodiment, from about 185 to about 380 grams per hectare of plant cell membrane disruptor is applied to the area in need of weed control. In a more preferred embodiment, from about 200 to about 365 grams per hectare of plant cell membrane disruptor is applied to the area in need of weed control. In a most preferred embodiment, from about 215 to about 350 grams per hectare of plant cell membrane disruptor is applied to the area in need of weed control.

In an embodiment, from about 132 to about 527 grams per hectare of fomesafen, or an agriculturally acceptable salt thereof, is applied to the area in need of weed control. In a preferred embodiment, from about 185 to about 380 grams per hectare of fomesafen, or an agriculturally acceptable salt thereof, is applied to the area in need of weed control. In a more preferred embodiment, from about 200 to about 365 grams per hectare of fomesafen, or an agriculturally acceptable salt thereof, is applied to the area in need of weed control. In a most preferred embodiment, from about 215 to about 350 grams per hectare of fomesafen, or an agriculturally acceptable salt thereof, is applied to the area in need of weed control.

In an embodiment, from about 105 to about 440 grams per hectare of lactofen, or an agriculturally acceptable salt thereof, is applied to the area in need of weed control. In a preferred embodiment, from about 185 to about 380 grams per hectare of lactofen, or an agriculturally acceptable salt thereof, is applied to the area in need of weed control. In a more preferred embodiment, from about 200 to about 365 grams per hectare of lactofen, or an agriculturally acceptable salt thereof, is applied to the area in need of weed control. In a most preferred embodiment, from about 200 to about 250 grams per hectare of lactofen, or an agriculturally acceptable salt thereof, is applied to the area in need of weed control.

In another embodiment of the invention, flumiclorac-pentyl is also applied to the area in need of weed control. In an embodiment, from about 10 to about 150 grams per hectare of flumiclorac-pentyl is applied to the area in need of weed control. In a preferred embodiment, from about 14 to about 116 grams per hectare of flumiclorac-pentyl is applied to the area in need of weed control. In a more preferred embodiment, from about 14 to about 90 grams per hectare of flumiclorac-pentyl is applied to the area in need of weed control. In a most preferred embodiment, from about 14.5 to about 73 grams per hectare of flumiclorac-pentyl is applied to the area in need of weed control.

In a further embodiment, the weed controlled by the compositions of the present invention is at least one of Waterhemp (*Amaranthus tuberculatus*), Horseweed (*Conyza Canadensis*), Ivyleaf Morningglory (*Ipomoea hederacea*), Pitted Morningglory (*Ipomoea lacunose*), Common Ragweed (*Ambrosia artemisiifolia*) Large Crabgrass (*Digitaria sanguinalis*), Palmer Amaranth (*Amaranthus palmeri*), Broadleaf Signalgrass (*Brachiaria platyhylla*), Common Barnyardgrass (*Echinochloa crus-galli*), Yellow Nutsedge (*Cyperus esculentus*), Eclipta (*Eclipta prostrate*), Lamb's quarters (*Chenopodium*), Velvetleaf (*Abutilon theophrasti*), and Giant Foxtail (*Setaria faberi*). In a preferred embodiment, the weed controlled is Waterhemp. In another preferred embodiment, the weed controlled is Common Ragweed. In yet another embodiment, the weed controlled is Ivyleaf Morningglory. In yet another embodiment, the weed controlled is Pitted Morningglory. In a further embodiment, the weed controlled is Horseweed. In another embodiment, the weed controlled is Velvetleaf.

In an embodiment of the invention, the pyroxasulfone and plant cell membrane disruptor herbicide, or an agriculturally acceptable salt thereof, are applied concurrently to the area in need of weed control. In another embodiment, the pyroxasulfone and plant cell membrane disruptor herbicide, or an agriculturally acceptable salt thereof, are applied sequentially to the area in need of weed control.

In a preferred embodiment, the plant cell membrane disruptor herbicide of the present invention is fomesafen, or an agriculturally acceptable salt thereof. In another preferred embodiment, the plant cell membrane disruptor of the present invention is the lactofen, or an agriculturally acceptable salt thereof.

Applicants' mixtures can be applied by any convenient means. Those skilled in the art are familiar with the modes of application that include foliar applications such as spraying, chemigation (a process of applying the mixture through the irrigation system), by granular application, or by impregnating the mixture on fertilizer.

Applicants' mixtures can be prepared as concentrate formulations or as ready-to-use formulations. The mixtures can be tank mixed.

The herbicide mixtures of the present invention may be formulated to contain adjuvants, such as solvents, anti-caking agents, stabilizers, defoamers, slip agents, humectants, dispersants, wetting agents, thickening agents, emulsifiers, and preservatives which increase the long lasting activity of the actives. Other components that enhance the biological activity of these ingredients may optionally be included.

Methylated seed oil ("MSO") is an adjuvant that improves leaf cuticle penetration of an agricultural active, such as a plant growth regulator, fungicide or herbicide. MSO can be used in the mixtures of the present invention, but is not required or responsible for the synergy of the combination the herbicides of the present invention. Other oil based adjuvants with similar qualities could also be used, such as crop oil concentrates.

Mixtures of the present invention can be formulated to contain a liquid solvent. Examples of solvents include water or oil concentrates.

Applicants' mixtures can also include one or more additional herbicides.

The mixtures of the present invention can be applied to any environment in need of weed control. The environment in need of weed control may include any area that is desired to have a reduced number of weeds or to be free of weeds. For example, the herbicide combination can be applied to an area used to grow crop plants, such as a field, orchard, or vineyard. For example, Applicants' compositions and methods can be applied to areas where soybeans, corn, peanuts, and cotton are growing. In a preferred embodiment, the mixture is applied in an area where a broadleaf crop (soybean, cotton, peanut, orchard, vineyard, forages) is growing. The mixtures of the present invention can also be applied to non-agricultural areas in need of weed control such as a lawns, golf courses, or parks.

Applicants' compositions and methods can be applied successfully to crop plants and weeds that are resistant to glyphosate, glufosinate, or other herbicides. The composition and methods can also be applied to areas where genetically modified crops ("GMOs") or non-GMO crops are growing. The term "GMO crops" as used herein refers to crops that are genetically modified.

When used in this application, Horseweed refers to *Conyza Canadensis*, Large Crabgrass refers to *Digitaria sanguinalis*, Palmer Amaranth refers to *Amaranthus palmeri*, Broadleaf Signalgrass refers to *Brachiaria platyhylla*, Common Barnyardgrass refers to *Echinochloa crus-galli*, Yellow Nutsedge refers to *Cyperus esculentus*, Eclipta refers to *Eclipta prostrate*, Giant Ragweed refers to *Ambrosia trifida*, Common Ragweed refers to *Ambrosia artemisiifolia*, Velvetleaf refers to *Abutilon theophrasti*, Waterhemp refers to *Amaranthus tuberculatus*, Ivyleaf Morningglory refers to *Ipomoea hederacea*, Pitted Morningglory refers to *Ipomoea lacunose*, and Common Ragweed refers to *Ambrosia artemisiifolia*.

Although the composition of the present invention has proven synergy when applied to Horseweed, Common Ragweed, Velvetleaf, Waterhemp, and Morningglory, the synergistic composition could be applied to any number of other weeds or undesired plants for effective control and is not limited to the examples.

Throughout the application, the singular forms "a," "an," and "the" include plural reference unless the context clearly dictates otherwise.

As used herein, "g ai/ha" is an abbreviation for grams of active ingredient per hectare.

As used herein, all numerical values relating to amounts, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

As used herein, "post emergence" refers to an herbicide treatment that is applied to an area after the weeds have germinated and emerged from the ground or growing medium.

As used herein, "burndown" refers to when an herbicide is used to reduce weed presence at the time of treatment. Burndown is often used in minimum or no-till fields because the weeds cannot be managed by tilling the soil. The burndown application may be used post-harvest and/or prior to crop emergence. Burndown is especially useful against weeds that emerge between growing seasons.

As used herein, synergy means that when combined, the claimed composition achieves a result that is greater than the expected result.

These representative embodiments are in no way limiting and are described solely to illustrate some aspects of the invention.

Further, the following example is offered by way of illustration only and not by way of limitation.

EXAMPLE

Example 1

The following field test was conducted in 2013 in the state of Iowa in the United States. Roundup Ready soybeans (*Glycine max*) were used in the test as the crop plant utilizing a natural population of weeds. All of the treatments contained MSO concentrate oil at 1% v/v and were applied at the V3 soybean growth stage. Applications were made utilizing a utility vehicle sprayer with application area for each treatment equating to 30 feet by 200 feet.

When the test began, the test plot had weeds that were 6 inches tall. Fomesafen was administered at 263 grams/hectare. Pyroxasulfone was administered at 90 grams/hectare.

On 14 days after treatment ("DAT"), readings were taken to determine the survival of Velvetleaf, Waterhemp, and Common ragweed. On 21 DAT, readings were taken to determine the residual control of Velvetleaf, Waterhemp, and Horseweed. Survival ratings were taken by counting the number of alive and dead plants at the time of the reading. All data was analyzed using Bartlett's test and with p value of 0.5 for determining significance of the results. The results of this study can be seen below in "Table 1. The Effect of Fomesafen and Pyroxasulfone on Weeds."

The results illustrate that a treatment of fomesafen and pyroxasulfone is more effective than fomesafen alone or fomesafen with S-metolachlor. The three-way treatment with fomesafen, pyroxasulfone, and flumiclorac was significantly more effective than fomesafen alone or fomesafen with S-metolachlor. The three-way mixture provided at least 97% kill or residual control of velvetleaf, waterhemp, ragweed, and horseweed. In contrast, the S-metolachlor and fomesafen treatment only provided 25% control of velvetleaf, 87% control of waterhemp, and 77% of common ragweed. The S-metolachlor and fomesafen treatment only provided 75% residual control of velvetleaf, 93% residual control of waterhemp, and 45% residual control of horseweed.

Example 2

The following field test was conducted in the state of Missouri in the United States in 2013. Roundup Ready soybeans (*Glycine max*) were used in the test as the crop plant. The treatments were applied at the V3 stage of soybean growth utilizing a backpack sprayer. Treatment area was 10 feet by 350 feet.

Waterhemp, Ivyleaf Morningglory, Pitted Morningglory, and Ragweed were evaluated 24, 53 and 64 days after the treatments. The results of these observations can be seen below in Tables 2 to 5. The soybeans were also evaluated at 29, 34, 53, and 64 days after treatments. No significant soybean phytotoxicity was observed.

TABLE 2

The Effect of Postemergence Plant Cell Membrane Disruptor Herbicides and Pyroxasulfone on Waterhemp

| Trt | Herbicide | Rates (g ai/ha) | 34 DAT | 53 DAT | 64 DAT |
|---|---|---|---|---|---|
| 1 | Glyphosate | 1340 | 67.8 | 67.5 | 31.3 |
|   | Ammonium sulphate | 7060 | | | |
| 2 | S-metolachlor | 1220 | 71.3 | 71.5 | 30 |
|   | Fomesafen | 266 | | | |
|   | Glyphosate | 1340 | | | |
|   | Ammonium sulphate | 7060 | | | |
| 3 | Lactofen | 219 | 86.5 | 78.5 | 55 |
|   | Pyroxasulfone | 90 | | | |
|   | Glyphosate | 1340 | | | |
|   | Ammonium sulphate | 7060 | | | |
|   | Crop Oil Concentrate | 2870 | | | |
| 4 | Lactofen | 219 | 74.8 | 78.8 | 50 |
|   | Pyroxasulfone | 119 | | | |
|   | Glyphosate | 1340 | | | |
|   | Ammonium sulphate | 7060 | | | |
|   | Crop Oil Concentrate | 2870 | | | |

TABLE 1

The Effect of Fomesafen and Pyroxasulfone on Weeds

| Trt | Herbicide | Rate (grams of ai per hectare) | Velvetleaf | Residual control of velvetleaf | Waterhemp | Residual control of waterhemp | Common ragweed | Horseweed (bolted) |
|---|---|---|---|---|---|---|---|---|
| 1 | S-metolachlor | 1220 | 25 | 75 | 87 | 93 | 77 | 45 |
|   | Fomesafen | 266 | | | | | | |
| 2 | Fomesafen | 263 | 78 | 97 | 67 | 97 | 80 | 50 |
| 3 | Fomesafen | 263 | 90 | 97 | 95 | 97 | 90 | 90 |
|   | Pyroxasulfone | 90 | | | | | | |
| 4 | Fomesafen | 263 | 100 | 97 | 97 | 97 | 97 | 97 |
|   | Pyroxasulfone | 90 | | | | | | |
|   | Flumiclorac | 28 | | | | | | |

TABLE 2-continued

The Effect of Postemergence Plant Cell Membrane Disruptor Herbicides and Pyroxasulfone on Waterhemp

| Trt | Herbicide | Rates (g ai/ha) | 34 DAT | 53 DAT | 64 DAT |
|---|---|---|---|---|---|
| 5 | Lactofen | 219 | 82.8 | 79.5 | 46.3 |
|  | Acetochlor | 1230 |  |  |  |
|  | Glyphosate | 1340 |  |  |  |
|  | Ammonium sulphate | 7060 |  |  |  |
|  | Crop Oil Concentrate | 2870 |  |  |  |
| 6 | Lactofen | 219 | 77 | 71.3 | 40 |
|  | S-metolachlor | 1460 |  |  |  |
|  | Glyphosate | 1340 |  |  |  |
|  | Ammonium sulphate | 7060 |  |  |  |
|  | Crop Oil Concentrate | 1400 |  |  |  |
| 7 | Lactofen | 219 | 56 | 72 | 41.3 |
|  | Glyphosate | 1340 |  |  |  |
|  | Ammonium sulphate | 7060 |  |  |  |
|  | Dimethenamid-P | 735 |  |  |  |
| 8 | Lactofen | 210 | 70.3 | 70 | 30 |
|  | Flumiclorac pentyl ester | 45 |  |  |  |
|  | Crop Oil Concentrate | 1400 |  |  |  |
|  | Glyphosate | 1340 |  |  |  |
|  | Ammonium sulphate | 7060 |  |  |  |
| 9 | Pyroxasulfone | 90 | 83.2 | 79 | 41.3 |
|  | Fomesafen, sodium salt | 342 |  |  |  |
|  | Glyphosate | 1340 |  |  |  |
|  | Ammonium sulphate | 7060 |  |  |  |
|  | Crop Oil Concentrate | 1400 |  |  |  |
| 10 | Fomesafen, | 342 | 85.6 | 81.3 | 43.8 |
|  | Glyphosate | 1100 |  |  |  |
|  | Ammonium sulphate | 7060 |  |  |  |
|  | Non-ionic Surfactant | 420 |  |  |  |
| 11 | Fomesafen | 175 | 62.5 | 69.5 | 54.3 |
|  | Fluthiacet methyl | 8 |  |  |  |
|  | Glyphosate | 1340 |  |  |  |
|  | Ammonium sulphate | 7060 |  |  |  |

TABLE 3

The Effect of Plant Cell Membrane Disruptor Herbicides and Pyroxasulfone on Ivyleaf Morningglory

| Trt | Herbicide | Rates (g ai/ha) | 34 DAT | 53 DAT | 64 DAT |
|---|---|---|---|---|---|
| 1 | Glyphosate | 1340 | 89.3 | 86.8 | 75 |
|  | Ammonium sulphate | 7060 |  |  |  |
| 2 | S-metolachlor | 1220 | 97 | 92.8 | 80 |
|  | Fomesafen | 266 |  |  |  |
|  | Glyphosate | 1340 |  |  |  |
|  | Ammonium sulphate | 7060 |  |  |  |
| 3 | Lactofen | 219 | 97.5 | 88.5 | 66.3 |
|  | Pyroxasulfone | 90 |  |  |  |
|  | Glyphosate | 1340 |  |  |  |
|  | Ammonium sulphate | 7060 |  |  |  |
|  | Crop Oil Concentrate | 2870 |  |  |  |
| 4 | Lactofen | 219 | 98 | 91.5 | 75 |
|  | Pyroxasulfone | 119 |  |  |  |
|  | Glyphosate | 1340 |  |  |  |
|  | Ammonium sulphate | 7060 |  |  |  |
|  | Crop Oil Concentrate | 2870 |  |  |  |
| 5 | Lactofen | 219 | 98 | 93.8 | 65 |
|  | Acetochlor | 1230 |  |  |  |
|  | Glyphosate | 1340 |  |  |  |
|  | Ammonium sulphate | 7060 |  |  |  |
|  | Crop Oil Concentrate | 2870 |  |  |  |
| 6 | Lactofen | 219 | 92 | 90.8 | 72.5 |
|  | S-metolachlor | 1460 |  |  |  |
|  | Glyphosate | 1340 |  |  |  |
|  | Ammonium sulphate | 7060 |  |  |  |
|  | Crop Oil Concentrate | 1400 |  |  |  |
| 7 | Lactofen | 219 | 95 | 94.5 | 75 |
|  | Glyphosate | 1340 |  |  |  |
|  | Ammonium sulphate | 7060 |  |  |  |
|  | Dimethenamid-P | 735 |  |  |  |
| 8 | Lactofen | 210 | 98 | 92.3 | 67.5 |
|  | Flumiclorac pentyl ester | 45 |  |  |  |
|  | Crop Oil Concentrate | 1400 |  |  |  |
|  | Glyphosate | 1340 |  |  |  |
|  | Ammonium sulphate | 7060 |  |  |  |
| 9 | Pyroxasulfone | 90 | 98.5 | 94.8 | 76.3 |
|  | Fomesafen, sodium salt | 342 |  |  |  |
|  | Glyphosate | 1340 |  |  |  |
|  | Ammonium sulphate | 7060 |  |  |  |
|  | Crop Oil Concentrate | 1400 |  |  |  |
| 10 | Fomesafen, | 342 | 95 | 86.3 | 62.5 |
|  | Glyphosate | 1100 |  |  |  |
|  | Ammonium sulphate | 7060 |  |  |  |
|  | Non-ionic Surfactant | 420 |  |  |  |
| 11 | Fomesafen | 175 | 97.5 | 94.5 | 88.8 |
|  | Fluthiacet methyl | 8 |  |  |  |
|  | Glyphosate | 1340 |  |  |  |
|  | Ammonium sulphate | 7060 |  |  |  |

TABLE 4

The Effect of Plant Cell Membrane Disruptor Herbicides and Pyroxasulfone on Pitted Morningglory

| Trt | Herbicide | Rates (g ai/ha) | 34 DAT | 53 DAT | 64 DAT |
|---|---|---|---|---|---|
| 1 | Glyphosate | 1340 | 84 | 84 | 75 |
|  | Ammonium sulphate | 7060 |  |  |  |
| 2 | S-metolachlor | 1220 | 97 | 95.3 | 80 |
|  | Fomesafen | 266 |  |  |  |
|  | Glyphosate | 1340 |  |  |  |
|  | Ammonium sulphate | 7060 |  |  |  |
| 3 | Lactofen | 219 | 95 | 88.5 | 66.3 |
|  | Pyroxasulfone | 90 |  |  |  |
|  | Glyphosate | 1340 |  |  |  |
|  | Ammonium sulphate | 7060 |  |  |  |
|  | Crop Oil Concentrate | 2870 |  |  |  |
| 4 | Lactofen | 219 | 96.8 | 94.3 | 75 |
|  | Pyroxasulfone | 119 |  |  |  |
|  | Glyphosate | 1340 |  |  |  |
|  | Ammonium sulphate | 7060 |  |  |  |
|  | Crop Oil Concentrate | 2870 |  |  |  |
| 5 | Lactofen | 219 | 93 | 94.5 | 65 |
|  | Acetochlor | 1230 |  |  |  |
|  | Glyphosate | 1340 |  |  |  |
|  | Ammonium sulphate | 7060 |  |  |  |
|  | Crop Oil Concentrate | 2870 |  |  |  |
| 6 | Lactofen | 219 | 98.5 | 90.8 | 72.5 |
|  | S-metolachlor | 1460 |  |  |  |
|  | Glyphosate | 1340 |  |  |  |
|  | Ammonium sulphate | 7060 |  |  |  |
|  | Crop Oil Concentrate | 1400 |  |  |  |
| 7 | Lactofen | 219 | 98 | 94.5 | 75 |
|  | Glyphosate | 1340 |  |  |  |
|  | Ammonium sulphate | 7060 |  |  |  |
|  | Dimethenamid-P | 735 |  |  |  |
| 8 | Lactofen | 210 | 96.5 | 90.8 | 67.5 |
|  | Flumiclorac pentyl ester | 45 |  |  |  |
|  | Crop Oil Concentrate | 1400 |  |  |  |
|  | Glyphosate | 1340 |  |  |  |
|  | Ammonium sulphate | 7060 |  |  |  |
| 9 | Pyroxasulfone | 90 | 95 | 95.5 | 76.3 |
|  | Fomesafen, sodium salt | 342 |  |  |  |
|  | Glyphosate | 1340 |  |  |  |
|  | Ammonium sulphate | 7060 |  |  |  |
|  | Crop Oil Concentrate | 1400 |  |  |  |
| 10 | Fomesafen, | 342 | 88.8 | 85 | 62.5 |
|  | Glyphosate | 1100 |  |  |  |
|  | Ammonium sulphate | 7060 |  |  |  |
|  | Non-ionic Surfactant | 420 |  |  |  |

TABLE 4-continued

The Effect of Plant Cell Membrane Disruptor
Herbicides and Pyroxasulfone on Pitted Morningglory

| Trt | Herbicide | Rates (g ai/ha) | 34 DAT | 53 DAT | 64 DAT |
|---|---|---|---|---|---|
| 11 | Fomesafen | 175 | 98.5 | 94.3 | 88.8 |
|  | Fluthiacet methyl | 8 |  |  |  |
|  | Glyphosate | 1340 |  |  |  |
|  | Ammonium sulphate | 7060 |  |  |  |

TABLE 5

The Effect of Plant Cell Membrane Disruptor
Herbicides and Pyroxasulfone on Ragweed

| Trt | Herbicide | Rates (g ai/ha) | 34 DAT | 53 DAT | 64 DAT |
|---|---|---|---|---|---|
| 1 | Glyphosate | 1340 | 80.8 | 90.5 | 66.3 |
|  | Ammonium sulphate | 7060 |  |  |  |
| 2 | S-metolachlor | 1220 | 98 | 97.3 | 82.5 |
|  | Fomesafen | 266 |  |  |  |
|  | Glyphosate | 1340 |  |  |  |
|  | Ammonium sulphate | 7060 |  |  |  |
| 3 | Lactofen | 219 | 99 | 97.8 | 77.5 |
|  | Pyroxasulfone | 90 |  |  |  |
|  | Glyphosate | 1340 |  |  |  |
|  | Ammonium sulphate | 7060 |  |  |  |
|  | Crop Oil Concentrate | 2870 |  |  |  |
| 4 | Lactofen | 219 | 91.8 | 95.8 | 85 |
|  | Pyroxasulfone | 119 |  |  |  |
|  | Glyphosate | 1340 |  |  |  |
|  | Ammonium sulphate | 7060 |  |  |  |
|  | Crop Oil Concentrate | 2870 |  |  |  |
| 5 | Lactofen | 219 | 92 | 90.5 | 65 |
|  | Acetochlor | 1230 |  |  |  |
|  | Glyphosate | 1340 |  |  |  |
|  | Ammonium sulphate | 7060 |  |  |  |
|  | Crop Oil Concentrate | 2870 |  |  |  |
| 6 | Lactofen | 219 | 98.5 | 96.8 | 73.8 |
|  | S-metolachlor | 1460 |  |  |  |
|  | Glyphosate | 1340 |  |  |  |
|  | Ammonium sulphate | 7060 |  |  |  |
|  | Crop Oil Concentrate | 1400 |  |  |  |
| 7 | Lactofen | 219 | 93.5 | 89.5 | 72.5 |
|  | Glyphosate | 1340 |  |  |  |
|  | Ammonium sulphate | 7060 |  |  |  |
|  | Dimethenamid-P | 735 |  |  |  |
| 8 | Lactofen | 210 | 97 | 94.3 | 77.5 |
|  | Flumiclorac pentyl ester | 45 |  |  |  |
|  | Crop Oil Concentrate | 1400 |  |  |  |
|  | Glyphosate | 1340 |  |  |  |
|  | Ammonium sulphate | 7060 |  |  |  |
| 9 | Pyroxasulfone | 90 | 99 | 97.8 | 81.3 |
|  | Fomesafen, sodium salt | 342 |  |  |  |
|  | Glyphosate | 1340 |  |  |  |

TABLE 5-continued

The Effect of Plant Cell Membrane Disruptor
Herbicides and Pyroxasulfone on Ragweed

| Trt | Herbicide | Rates (g ai/ha) | 34 DAT | 53 DAT | 64 DAT |
|---|---|---|---|---|---|
|  | Ammonium sulphate | 7060 |  |  |  |
|  | Crop Oil Concentrate | 1400 |  |  |  |
| 10 | Fomesafen, | 342 | 98.5 | 98.5 | 77.5 |
|  | Glyphosate | 1100 |  |  |  |
|  | Ammonium sulphate | 7060 |  |  |  |
|  | Non-ionic Surfactant | 420 |  |  |  |
| 11 | Fomesafen | 175 | 97 | 95 | 75 |
|  | Fluthiacet methyl | 8 |  |  |  |
|  | Glyphosate | 1340 |  |  |  |
|  | Ammonium sulphate | 7060 |  |  |  |

This study shows that the treatments of the present invention are safe for crop plants. It also shows that compositions of the present invention are effective against Waterhemp, Common Ragweed and Morningglory species.

What is claimed is:

1. An agricultural composition for controlling horseweed comprising an active ingredient consisting of fomesafen or an agriculturally acceptable salt thereof, and pyroxasulfone in a synergistic ratio of from about 1:0.4 to about 1:0.26.

2. An agricultural composition comprising for controlling horseweed an active ingredient consisting of fomesafen or an agriculturally acceptable salt thereof, and pyroxasulfone in a synergistic ratio of 1:0.34.

3. A method of increasing the activity of fomesafen comprising applying an agricultural composition comprising an active ingredient consisting of fomesafen or an agriculturally acceptable salt thereof, and pyroxasulfone in a synergistic ratio of from about 1:0.4 to about 1:0.26 to an area in need of horseweed control.

4. The method of claim 3 wherein the pyroxasulfone is applied at a rate of from about 50 to about 150 grams per hectare.

5. The method of claim 3 wherein the fomesafen is applied at a rate of from about 150 to about 400 grams per hectare.

6. The method of claim 3 wherein the fomesafen, or agriculturally acceptable salt thereof, and pyroxasulfone are applied concurrently or sequentially to the area in need of horseweed control.

7. The method of claim 3, wherein the synergistic ratio is about 1:0.34.

* * * * *